United States Patent [19]

Komai et al.

[11] 4,137,252
[45] Jan. 30, 1979

[54] DICYCLODODECYL PEROXYDICARBONATE

[75] Inventors: Takeshi Komai, Aichi; Kazuo Matsuyama, Gamagori; Kazuhiro Mizuno, Aichi, all of Japan

[73] Assignee: Nippon Oil and Fats Co., Ltd., Tokyo, Japan

[21] Appl. No.: 804,869

[22] Filed: Jun. 9, 1977

[30] Foreign Application Priority Data

Jun. 16, 1976 [JP] Japan ............................. 51/69719

[51] Int. Cl.² .......................................... C07C 179/18
[52] U.S. Cl. .................................. 260/463; 260/861; 526/230
[58] Field of Search ................................... 260/463

[56] References Cited

U.S. PATENT DOCUMENTS 3,720,700  3/1973  Norback .......................... 260/463
3,821,273  6/1974  D'Angelo ......................... 260/463

*Primary Examiner*—Elbert L. Roberts
*Assistant Examiner*—Molly C. Eakin
*Attorney, Agent, or Firm*—Blanchard, Flynn, Thiel, Boutell & Tanis

[57] ABSTRACT

Dicyclododecyl peroxydicarbonate of the formula:

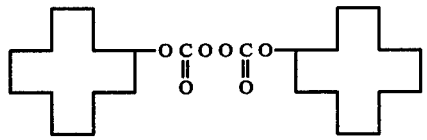

is stable and can be stored at room temperature. It has a high solubility in organic solvents and good compatibility with unsaturated polyester resins.

This compound is an improved polymerization initiator for free radical polymerizations of ethylenically unsaturated monomers, including copolymerization with monomers capable of copolymerizing therewith.

This compound also is a catalyst for curing unsaturated polyester resin compositions.

1 Claim, No Drawings

DICYCLODODECYL PEROXYDICARBONATE

BACKGROUND OF THE INVENTION

1. Field of the Invention

This invention relates to dicyclododecyl peroxydicarbonate having the following formula, which can be stored at room temperature for a long time and transported at room temperature. It is useful as a polymerization initiator for ethylenically unsaturated monomers and as a curing catalyst of unsaturated polyester resin compositions.

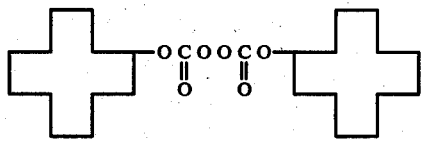

2. Description of the Prior Art

F. Strain discloses in U.S. Pat. No. 2,370,588 and Journal of American Chemical Society Vol. 72, 1254–1263 (1950) a process for preparing peroxydicarbonates including IPP (diisopropyl peroxydicarbonate), that they are useful as polymerization initiators which are active at a low temperature in the polymerization of ethylenically unsaturated monomers such as ethylene, styrene, methyl methacrylate, vinyl chloride and the like, and further, dicyclohexyl peroxydicarbonate is mentioned as a dialkyl peroxydicarbonate having cycloalkyl groups. The described peroxydicarbonates have the disadvantage in that they must be cooled during use or storage.

Japanese patent publication No. SHO 43-17572 discloses that 4-substituted dicyclohexyl peroxydicarbonates, for example, di-(4-tertiary butylcyclonexyl) peroxydicarbonate is stable at room temperature and accordingly it does not need to be frozen or stabilized during transportation and storage.

Japanese patent publication No. SHO 47-3970 also discloses that di-(cis - 3,3,5 - trimethylcyclohexyl) peroxydicarbonate is stable at room temperature.

Further, Japanese Patent Publication No. SHO 47-3971 discloses that di-(bicycloalkyl) peroxydicarbonates such as dibornyl peroxydicarbonate are stable at room temperature.

It is an object of the present invention to provide a non-substituted dicycloalkyl peroxydicarbonate which needs no cooling during handling or during storage.

It is another object of the present invention to provide a non-substituted dicycloalkyl peroxydicarbonate which possesses better solubility in organic solvents better the compability with unsaturated polyester resins in comparison with the commercially available peroxydicarbonates and which can cure unsaturated polyester resin compositions easily.

It is still another object of the present invention to provide a non-substituted dicycloalkyl peroxydicarbonate which is high in polymerization activity when it is used as a polymerization initiator.

It is another object of the present invention to provide a non-substituted cycloalkyl peroxydicarbonate which gives good characteristics to the obtained polymers.

The inventors completed this invention on the basis of the discovery that dicyclododecyl peroxydicarbonate, a novel compound, can be produced by reacting cyclodecyl chloroformate with hydrogen peroxide in the presence an alkali and that the thus obtained compound is stable at room temperature so that it can be stored for a long time without spontaneous combustion, and that the said compound has good solubility in organic solvents and good compatibility with unsaturated polyester resins, and is useful as a polymerization initiator possessing very high polymerization activity.

The said novel compound, of which the melting point is 76°–78° C. (decomposes at 77°–78° C.), is solid at room temperature.

This compound loses its assay only 6.6% when it is kept at a temperature of 30° C. for 3 weeks and only 7.0% when it is kept at 40° C. for a week.

The characteristic absorptions in the infrared spectrum of this compound were observed at 1790 cm$^{-1}$ ($v$ c=o) and 895 cm$^{-1}$ ($v$ o — o) corresonding to the characteristic absorptions of the peroxycarbonyl group.

In the nuclear magnetic resonance spectrum of this compound (solvent; CCl$_4$, standard material;tetramethylsilane), an absorption band of methylene protons was observed at 1.39 of $\delta$ (singlet), an absorption band of 8 $\beta$-methylene protons at 1.62–2.38 of $\delta$ (multiplet) and an absorption band of 2 $\alpha$-methylene protons at 4.76–5.12 of $\delta$ (multiplet).

Notwithstanding that dicyclododecyl peroxydicarbonate of the present invention is a solid crystal, the said compound has the advantage in that the solubilities thereof in organic solvents are so high that it can be dissolved in a small quantity of organic solvent when it is used in the form of a solution in the organic solvent.

Further it has another advantage in that when it is used as a curing catalyst for unsaturated polyester resins, the time for mixing the resins and the catalyst can be shortened, in comparison with a commercially available peroxydicarbonate that is stable at room temperature.

Polymerization

Dicyclododecyl peroxydicarbonate has splendid initiation activity as a free radical polymerization, and copolymerization, initiator of ethylenically unsaturated monomers.

Illustrative of the ethylenically unsaturated monomers are ethylene, styrene, $\alpha$-methylstyrene, dichlorostyrene, p-chlorostyrene, vinylnaphthalene, vinylphenol, vinyltoluene, divinylbenzene, acrylic acid, $\alpha$-alkyl substituted acrylic acid such as methacrylic acid, esters of unsaturated acids such as methyl acrylate, methyl methacrylate, butyl methacrylate, propyl acrylate, ethyl acrylate and 2 - ethylhexyl acrylate; amides of unsaturated acids such as acrylamide and methacrylamide; vinylidene halides such as vinylidene chloride, vinylidene bromide and vinylidene fluoride; vinyl esters of inorganic acids such as vinyl chloride, vinyl fluoride, vinyl bromide, acrylonitrile and methacrylonitrile; vinyl esters such as vinyl acetate, vinyl chloroacetate, vinyl benzoate, vinyl valerate, vinyl caproate, vinyl propionate, divinyl succinate, divinyl adipate, vinyl allyl phthalate, vinyl methallyl pimelate, vinyl methyl glutarate, vinyl acrylate, vinyl crotonate and vinyl methacrylate; vinyl ethers such as vinyl ethyl ether, vinyl butyl ether, vinyl allyl ether and vinyl methallyl ether; vinyl ketones such as vinyl ketone and vinyl ethyl ketone; allyl derivatives such as allyl acetate, allyl butyrate, diallyl phthalate, diallyl adipate, methallyl propionate, allyl chloride, methallyl chloride, allyl acrylate, methallyl methacrylate and diallyl carbonate; conjugated dienes such as butadiene, chloroprene, isoprene and acrolein; maleic anhydride, maleic acid, fumaric acid and esters thereof; perhalo olefins such as tetrafluoroethylene, hexafluoroprpoylene, and chlorotrifluoroethylene.

A preferred monomer is vinyl chloride. Polymerization of vinyl chloride is carried out at about 30°–80° C., perferably 55°–65° C., using 0.003–0.300% or more by weight (preferably 0.01°–0.20% by weight) of dicyclododecyl peroxydicarbonate, based on the polymerizable monomer.

Dicyclododecyl peroxydicarbonate of the present invention has advantages as a polymerization initiator in that the initiation activity thereof is high, especially at a polymerization temperature of about 55°–65° C., and that the obtained vinyl chloride polymer has a little initial coloration and fish eyes therein.

The heretofore known solid peroxydicarbonates do not have such advantages. The novel compound of the present invention contributes much to the vinyl chloride industry.

Curing of Polyester Resins

Dicyclododecyl peroxydicarbonate of the present invention may be used as a catalyst for curing unsaturated polyester resin compositions at elevated temperatures.

It has been known that unsaturated polyester resin compositions can be cured by using peroxydicarbonates faster at low temperature, in comparison with dibenzoyl peroxide that is used conventionally in the same industry.

The peroxydicarbonates that are stable at room temperature have the disadvantage that it takes much time to admix the catalyst with the unsaturated polyester resin compositions, because the catalyst is a solid crystal and the solubility thereof in unsaturated polyester resin compositions is very small.

On the contrary, dicyclododecyl peroxydicarbonate according to the present invention, shortens the time needed for the mixing process, because its solubility in unsaturated polyester resin compositions is high.

The above mentioned unsaturated polyesters can be obtained by esterifying one or more ethylenically unsaturated di - or, poly - carboxylic acids or anhydrides thereof such as maleic acid, fumaric acid, glutaconic acid, itaconic acid, mesaconic acid, citraconic acid, allyl malonic acid, allyl succinic acid with saturated or unsaturated polyalcohols such as ethyleneglycol, diethyleneglycol, triethyleneglycol, propanediol-1,2,butanediol-1,3, 2,2-dimethyl propanediol-1,3, 2-butenediol-1,4, glycerin, pentaerythritol and mannitol.

A mixture of the acid and the alcohol as mentioned in the foregoing may be used. The unsaturated di-or polycarboxylic acids may be replaced partially with saturated carboxylic acids such as adipic acid, succinic acid and sebacic acid, or aromatic dibasic acids or anhydrides thereof such as phthalic acid and tetrahydrophthalic acid. The acids as well as the alcohols may be substituted with other groups (preferably halogen). Illustrative of the halogenated acids are tetrachlorophthalic acid and 1,4,5,6,7, 7-hexachlorobicyclo[2,2,1]heptene - $\Delta^5$, 2,3-dicarboxylic acid.

The other components of the unsaturated polyester resin compositions are unsaturated monomers which are copolymerizable ethylenically unsaturated monomers such as styrene, vinyltoluene, methyl methacrylate, diallyl phthalate, dibutyl fumarate, acrylonitrile, triallyl cyanurate, α-methylstyrene, divinyl benzene, methyl acrylate, diallyl maleate, η-butyl methacrylate, ethyl acrylate and the like.

The preferred resin compositions contain, as the polyester component, the esterification product of propylene glycol (a polyalcohol), maleic anhydride (anhydride of an unsaturated dicarboxylic acid) and phthalic anhydride (anhydride of an aromatic dicarboxylic acid) and, as the monomer component, styrene.

0.05–5.0 weight parts of dicyclododecyl peroxydicarbonate of the present invention is added into 100 weight parts of the unsaturated polyester resin composition.

The resultant mixture is heated at a temperature of about 20°–100° C. whereby the resin can be cured.

REFERENCE EXAMPLE-1

(Storage Safety)

The respective peroxydicarbonates as shown in Table 1 were placed in a thermostat kept at a temperature of 30° or 40° C. The amount of the active oxygen of the respective peroxydicarbonate was measured at fixed intervals to measure the percent loss of the respective assay and the obtained results are shown in Table 1.

It is recognized from Table 1 that dicyclododecyl peroxydicarbonate of the present invention was stable at a temperature of 30° C. for one or three weeks, but on the contrary diisopropyl-, dicyclohexyl-, and di-n-dodecylperoxydicarbonates lost all of their activities at 30° C. within 2 weeks and in fact diisopropyl peroxydicarbonate decomposed violently at 30° C. after 10–15 minutes.

Further it was ascertained that di-(tert-butylcyclohexyl) peroxydicarbonate decomposed at 40° C. more violently than dicyclododecyl peroxydicarbonate of the present invention.

Table 1

| Peroxydicarbonate | Thermal stability | | | | |
|---|---|---|---|---|---|
| | Melting point °C | Percent loss of assay (%) | | | |
| | | 30° C. 1 week | 30° C. 2 weeks | 30° C. 3 weeks | 40° C. 20 days |
| Dicyclododecyl peroxydicarbonate | 78 | 2.1 | 4.8 | 6.6 | 21.8 |
| Diidopropyl peroxydicarbonate | 8–10 | 100 | 100 | 100 | 100 |
| Dicyclohexyl peroxydicarbonate. | 47 | 13.1 | 100 | 100 | 100 |
| Di-n-dodecyl peroxydicarbonate | 29–30 | 21.7 | 100 | 100 | 100 |
| Di-(4-tert-butylcyclohexyl) peroxydicarbonate | 85 | 0.2 | 0.7 | 0.8 | 56 |

REFERENCE EXAMPLE 2

(Solubility in Organic Solvents)

The solubility of the respective peroxydicarbonate in the organic solvents at 5° C. was measured and the obtained results are shown in Table 2.

Table 2

| Dialkylperoxydicarbonate | Solubility of dialkyl peroxydicarbonate at 5° C. (g/solvent 100 g) | | |
|---|---|---|---|
| | | toluene | n-hexane | ethylene dichloride |
| This invention Reference | Dicyclododecyl peroxydicarbonate | 68.4 | 10.5 | 51.7 |
| | Di-(4-tert- | | | |

Table 2-continued

| Dialkylperoxy-dicarbonate | | Solubility of dialkyl peroxydicarbonate at 5° C. (g/solvent 100 g) | | |
|---|---|---|---|---|
| | | toluene | n-hexane | ethylene dichloride |
| Reference | butyl cyclohexyl peroxy-dicarbonate | 45.3 | 5.03 | 45.3 |
| | Di-n-hexadecyl peroxy-dicarbonate | 9.64 | 1.21 | 1.54 |

It is recognized from Table 2 that notwithstanding that dicyclododecyl peroxydicarbonate is a solid crystal, its solubility in organic solvents is larger than that of the other peroxydicarbonates which are stable at room temperature.

It is ascertained from the above fact that the compound of the present invention has an advantage in that when it was used in the form of a solution, a little quantity of the organic solvent is sufficient for dissolving it and another advantage in that when it was used as a catalyst for curing unsaturated polyester resin composition, the time for mixing the compositions with the catalyst could be shortened.

EXAMPLE 1

(Preparation of Dicyclododecyl Peroxydicarbonate)

27.7 g of cyclododecyl chloroformate (0.10 mole,) was dissolved into 40 ml. of isopropyl alcohol. The resultant solution was kept at 20±2° C. Into the solution, 4.1 g of 50% aqueous solution of hydrogen peroxide (0.06 mole) was added. The obtained solution was maintained, with stirring, at 20±2° C. for 20 minutes. Then 20.2 g of 20 wt % aqueous solution of sodium hydroxide was added into the solution at 20 + 2° C. for 20 minutes. Further the resultant mixture was heated at 30 + 2° C. and then stirring was continued at the same temperature for 2 hours. The obtained mixture was poured into 800 ml. of cold water. The precipitate was filtered off, washed with water and then with methanol, and dried. 20.4g of raw product was obtained.

(yield: 89.1%)

The amount of active oxygen was 3.49% (the assay of the raw product was; 99.1%)

The raw product was recrystallized in ethyl acetate whereby 17.8 g of purified crystals (yield: 77.3%) was obtained. The amount of active oxygen was 3.47% (the assay of the purified product was 98.6%). The amount of chlorine was 0.0933% (the content of the said chloroformate was 0.65%). The melting point of the product was 76°-78° C. and the decomposition point was 77°-78° C. The characteristic absorptions of the infrared absorption spectrum of the product were observed at 1790 cm$^{-1}$ ($\nu$ c=o) and 895 cm$^{-1}$ ($\nu$ o — o).

The results of the nuclear magnetic resonance spectrum of this compound were as follows.

$\delta$: 1.39 (s, 36H, methylene proton)
1.62–2.38 (m. 8H, $\beta$-methylene proton)
4.76–5.12 (m. 2H, $\alpha$-methylene proton)

EXAMPLE 2

(Vinyl chloride Suspension Polymerization Efficiency of Peroxydicarbonates)

Vinyl chloride suspension polymerizations were run at 60° C. for 8 hours in order to determine the amounts of initiators required for 80% conversion of vinyl chloride. The following recipe was employed in these polymerizations.

| Ingredients | Parts by weight |
|---|---|
| Vinyl chloride monomer | 100 |
| Water (boiled ion-exchanged water) | 300 |
| Gohsenol (GH - 17)* | 0.45 |
| Free radical initiator | variable |

*Trade mark of polyvinyl alcohol (saponification value 86.5 – 89 mol %) produced by Nihon Gosei Chemicals Co. Ltd.

Autoclaves of 42 mm in diameter and 230 mm in height which were made of stainless steel were used for the polymerizations. Into the autoclave, an aqueous solution of Gohsenol, which was obtained by dissolving it into the water, was added. Then the autoclaves were maintained at −60∼ −50° C. Into each autoclave a variable quantity of a free radical initiator as shown in Table 2 and 100 parts by weight of liquid vinyl chloride monomer were added at a temperature of −60∼ −50° C. Then the autoclaves were placed into a thermo-polymerization container that was maintained at 60° C. The thermo-polymerization container was rotated at 32 rpm whereby the polymerization was carried out. The autoclave was taken out from the thermo-polymerization container every hour from the start of the polymerization to check the polymerization conversion. None of the examples took more than 10–15 minutes to discharge unreacted vinyl chloride monomers, because post polymerization was insignificant. The amount of the obtained polymers was determined gravimetrically.

Regarding the respective initiators, the product of the time for polymerization multiplied by the square root of the concentration of the initiator were plotted against the conversion. The amount of the initiator (in grams and in moles) required for 80% conversion for 8 hours at 60° C. was obtained from the obtained plot. The results are shown in Table 3.

Table 3

| | Suspension Polymerization of Vinyl Chloride at 60° C. for 8 Hours | |
|---|---|---|
| | Dialkylperoxy-dicarbonate | Amount of initiator per 100 g of vinyl chloride required for at 80% conversion |
| This invention | Dicyclododecyl-peroxy dicarbonate | 0.049 g (1.08 10$^{-4}$ mole) |
| Reference | Di-n-hexadecyl-peroxy dicarbonate | 0.124 g (2.16 10$^{-4}$ mole) |
| Reference | Di-(4-tert-butyl cyclohexyl)peroxy dicarbonate | 0.095 g (2.40 10$^{-4}$ mole) |
| Reference | Dibornylperoxy dicarbonate | 0.084 g (2.14 10$^{-4}$ mole) |

Table 3 shows that the cyclododecyl peroxydicarbonate of the present invention is more effective than the reference peroxydicarbonates which are stable at room temperature. Then it was recognized that the dicyclododecyl peroxydicarbonate is not only better in thermal stability but also is more effective for the polymerization of vinyl chloride than the reference dialkyl peroxydicarbonates.

REFERENCE EXAMPLE 3

(Initial Coloration and Fish eyes)

The characteristics of initial coloration and fish eyes of polyvinyl chloride resins which were produced in Table 3 were compared. The respective polyvinyl chlorides were admixed with the other ingredients as shown in Table 4.

Table 4.

| Ingredients | Part by weight |
|---|---|
| Polyvinyl chloride (less than 48 meshes) | 100 |
| Dioctyl phthalate | 50 |
| TVS # N 2000 - C* | 5 |
| Stearic acid | 3 |

*Stabilizer of dibutyl stannic maleate (Produced by Nitto Kasei Co. Ltd)

The thus admixed and blended polymers were rolled under the below mentioned conditions to thereby make sheets.

|  | Temperature | Duration of time |
|---|---|---|
| Roll | 150 – 160° C. | 5 minutes |
| Press | 160° C. | 3 minutes |

The color states of the obtained sheets were shown as the initial coloration. Also the sheets were pressed under the below mentioned conditions to thereby make boards of 1 mm in thickness. The number of fish eyes per $dm^2$ of the boards therein was measured. The obtained results are shown in Table 5.

Table 5

| | Initial coloration and Fish eyes | |
|---|---|---|
| Dialkyl peroxydicarbonate | Initial coloration | Number of fish eyes per $dm^2$ |
| This invention | Dicyclododecyl-peroxy dicarbonate | pale pink | 1.5 |
| Reference | Di-(4-tert-butyl-cyclohexyl) peroxy dicarbonate | pink | 3.1 |
| Reference | Di-n-hexadecyl-peroxy dicarbonate | pink | 3.1 |
| Reference | Dibornylperoxy dicarbonate | pale pink | 10.0 |

EXAMPLE 3

(SPI Exthothermic Reaction of Peroxydicarbonates)

Cure characteristics of the dicyclododecyl peroxydicarbonate of the present invention were determined in an unsaturated polyester resin. The basic unsaturated polyester resin used in this example was a mixture of unsaturated polyester and styrene monomer. The unsaturated polyester was an alkyd resin which was produced by esterifying a mixture consisting of the below mentioned ingredients. 0.0168 wt % of hydroquinone inhibiter, based on the weight of the thus obtained resin, was added therein.

| Ingredients | weight |
|---|---|
| Maleic anhydride | 0.795 mole |
| Phthalic anhydride | 1.202 mole |
| Propylene glycol | 2.195 mole |

The alkyd resin had an acid value of 40–50. 63 weight parts of the above mentioned unsaturated polyester resin (alkyd resin) was diluted with 37 weight parts of styrene monomer.

Gelation and cure characteristics of various catalysts in the unsaturated polyester resin was determined using the Standard SPI Exotherm procedure ("SPI Procedure for Running Exotherm Curves - Polyester Resins," published in the Preprint of the 16th Annual Conference - Reinforced Plastics Division Society of the Plastic Industry, Inc., February 1961).

Using this procedure at 82° C., the dicyclododecyl peroxydicarbonates of this invention was employed to cure the basic unsaturated polyester resin. Levels of peroxides equivalent in "active oxygen" content to 1 percent by weight of curable resin of dibenzoyl peroxide (industry standard) were employed. The SPI Exotherm data for the dicyclododecyl peroxydicarbonate of this invention and the peroxydicarbonate of the references are shown in Table 6.

It is recognized that the dicyclododecyl peroxydicarbonate of this invention has a high compatibility in the resin so that it is more easy to mix it with the resin so in comparison with other peroxydicarbonates which are stable at room temperature.

Table 6

| | SPI Exothermic Reaction of Dialkyl peroxydicarbonate at 82° C | | | | |
|---|---|---|---|---|---|
| Dialkyl peroxy-dicarbonate | | Gel. time (min) | Cure. time (min) | Peak exo. (° C.) | Time for dissolving in resin(min) |
| This invention | Dicyclododecyl peroxydicarbonate | 0.85 | 2.1 | 201 | 4 |
| | Di-(4-tert cyclohexyl) peroxydicarbonate | 0.70 | 2.0 | 194 | 8 |
| Reference | Di-n-hexadecyl peroxydicarbonate | 0.85 | 2.6 | 168 | 10 |
| | Dibornyl peroxydicarbonate | 0.85 | 1.9 | 192 | 7 |
| | Dibenzyl peroxydicarbonate | 1.1 | 3.1 | 150 | 30 |

What is claimed is:

1. Dicyclododecyl peroxycarbonate of the formula

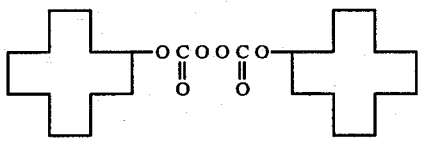

* * * * *